United States Patent [19]

Luby et al.

[11] Patent Number: Plant 7,197

[45] Date of Patent: Mar. 20, 1990

[54] APPLE TREE: HONEYCRISP

[75] Inventors: Jim Luby, St. Paul; David S. Bedford, Delano, both of Minn.

[73] Assignee: Regents of the University of Minnesota, Minneapolis, Minn.

[21] Appl. No.: 268,363

[22] Filed: Nov. 7, 1988

[51] Int. Cl.[4] ..... A01H 5/00

[52] U.S. Cl. ..... Plt./34

[58] Field of Search ..... Plt./34

[56] References Cited

PUBLICATIONS

Hoover, E. et al, "Apples for Minnesota", Minnesota Extension Service Publication AG-FO-1111, 1987, pp. 1-3.

*Primary Examiner*—James R. Feyrer

*Attorney, Agent, or Firm*—Merchant, Gould, Smith, Edell, Welter & Schmidt

[57] ABSTRACT

An apple tree having a slightly upright form with moderately vigorous growth; a superior fruit with solid to mottled red color over a yellow background and a crisp and juicy fruit texture; an extended season of harvest but with generally even ripening of fruit so that repeat pickings are unnecessary; good hardiness with little winter injury when grown near Excelsior, Minn. at approximately 45° latitude; and having annual fruit production with no flower thinning required.

2 Drawing Sheets

BACKGROUND INFORMATION

This invention is a new and distinct variety of apple tree. It was discovered by Applicant in September 1974 as part of the University of Minnesota apple breeding program to develop winter hardy varieties with high fruit quality.

This new cultivar is a seedling of known parentage planted in 1962 in block 53 of the University of Minnesota Horticultural Research Center, located in Carver County near Excelsior, Minn. In this seedling orchard the position of the tree was Row 1 Tree 88. The variety was produced from the cross number AE 603, Macoun x Honeygold. Following discovery and asexual reproduction by grafting, it was further tested as selection or designation MN 1711. This new cultivar is named HONEYCRISP.

The variety is most notable for its extremely crisp texture which is maintained for at least 5 months in storage at 34° F. without atmosphere modification. The fruit of Honeycrisp has been rated superior to fruit of McIntosh, Haralson, Honeygold, Regent, Delicious, and Keepsake by sensory evaluation panels for flavor and texture traits in winter storage tests (Chart A). Another advantage of this cultivar is that the season of harvest may be extended over a longer period compared to most current varieties, if desired. The acceptable harvest date may range from September 10 to October 15 at Excelsior, Minn. Fruit from the earlier harvest dates are generally mild in flavor while fruit from later harvest dates may be strongly aromatic. The average optimum harvest date is during the fourth week of September; approximately 5 days after McIntosh. The fruit on a tree ripens evenly and does not drop prematurely or after the optimum harvest period. Thus, the wide range of possible harvest dates does not imply that repeated pickings are required.

This new variety is also characterized by a moderately vigorous tree with a slightly upright growth habit. Trees bear fruit annually and do not require chemical or hand thinning. The variety has been hardy in the field at the above-noted location at Excelsior, Minn. with trees showing little winter injury and bearing fruit annually.

Laboratory freezing tests of 1-year old wood conducted in December 1986 and January 1988 compared Honeycrisp to other common varieties for cold hardiness (Chart B). Honeycrisp showed less freezing damage than regent, Honeygold and Haralson in the December 1986 test and in similar tests in January 1988 Honeycrisp showed less injury than McIntosh and Honeygold, but more injury than Regent and Harlson.

The fruit of this variety has an exceptionally crisp and juicy texture, with a sub-acid flavor and mild aroma. The skin has 50–90% solid to mottled red coloration over a yellow background with greater coloration if the fruit is more exposed to the sun. Lenticels are small and numerous. The fruit surface has shallow dimples and green russeting at the stem end. The flesh is cream colored and coarse in texture.

This new cultivar has been asexually reproduced by means of budding at the above-noted location in Excelsior, Minn. Examination of various trees of the cultivar has confirmed that the combination of characteristics described herein are firmly fixed through successive generations.

DESCRIPTION OF THE DRAWINGS

This new variety of apple tree is illustrated by the accompanying photographic drawings.

FIG. 1 is a photographic print in full color showing the form of a mature tree and the ripe fruit.

FIG. 2 is a photographic print in full color showing the mature fruit on a section of the tree.

Figure 3:
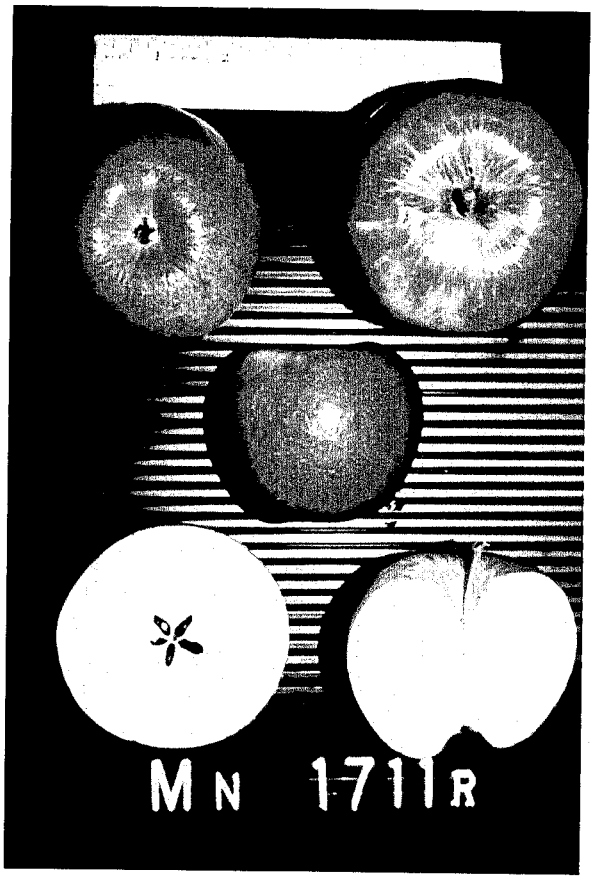
FIG. 3 is a photographic print in full color showing the fruit of this cultivar.

All photographs were taken in September at the University of Minnesota Horticultural Research Center, Excelsior, Minn.

DESCRIPTION OF THE NEW TREE

The following traits have been repeatedly observed and are believed to be characteristics of this cultivar which, in combination, distinguish this apple tree as a new and distinct cultivar.

The following is a detailed description of the new variety with the color designations according to the Horticultural Colour Chart issued by the British Colour Council in collaboration with The Royal Horticultural Society (Copyright 1938).

THE TREE

Habit: Slightly upright.
Bark: Smooth, bronze with prominent lenticels.

LEAF

Color: Spinach green (o960 to o960/1) and glossy on top, bottom is pubescent, spinach green (o960/3). Leaves are sometimes tinged yellow at the margins in late summer.
Shape: Ovate, serrate margin.
Aspect: Pubescent on bottom, top is smooth with puberulent veins.
Size: Length from 8.0 to 10.5 cm; width from 5 to 8 cm. Petiole: 3.0 to 3.5 cm in length.

FLOWER

Pedicel: Length 2.5 to 3.0 cm.
Corolla: 3.0 to 3.5 cm diameter; petal length/width ratio is 9:5.
Color: Open flower is Naples Yellow (plate 403/3).

The variety has been observed to produce up to 5% fruit set with self pollination in controlled pollination tests, but cross pollination is desirable for commercial production. In controlled cross pollinations, all varieties which have been used as pollinizers (such as Cortland, Fireside, Priscilla, Liberty, Freedom, and Redfree) have been successful in producing fruit set. Pollen is believed to be viable as it has successfully produced fruit on other varieties with which it has been used in cross breeding.

FRUIT

Shape: Oblate to roundly oblate; slightly irregular.
Size: Axial diameter 7.0 to 8.5 cm; transverse 6.0 to 7.0 cm.
Color: Blotched scarlet (plate 19) over lemon yellow (plate 4/2) background color.
Skin: Dimpled; dull; medium thick; dots are small, conspicuous, smooth and numerous. The skin is relatively thin and allows easy penetration when eating the fruit. As the flesh is macerated by chewing, the skin does have a slightly tough texture. Formation of a scarfskin has not been observed.
Stem: 3 cm long; 0.2 cm wide; medium thickness; stiff.
Cavity: Acute, medium depth and width; russetted.
Basin: Broad, deep.
Calyx: Persistent; mostly closed; slightly recurved.
Calyx tube: Conic.
Stamens: Median.
Core lines: Meeting; turbinate.
Core: Closed, medium large; broad.
Carpels: Ovate; smooth.
Seeds: Acuminate; not tufted.
Flesh:
*Texture.*—Coarse grained, extremely crisp, juicy.
*Flavor.*—Sub-acid, mildly aromatic.
*Color.*—Aureolin yellow (plate 3/3).
*Aroma.*—Mild, pleasant.
The fruit has not shown a tendency to bruise easily during routine picking and handling procedures.

Maturity season: September 10 to October 15 at Excelsior, Minn. Optimum time is 5 days after McIntosh.
Diseases: The variety is slightly susceptible to apple scab. Symptoms of Cedar Apple Rust and Fireblight, other diseases occurring in the Minnesota area, have not been observed on this variety, but the resistance status for such diseases is generally unknown. The virus status of the variety is unknown.
Storage ability: Retains quality and texture for up to 5 months at 34° F. in nonmodified atmosphere.
Use: The variety has excellent quality for dessert or fresh consumption use. It also has good quality for home processing uses including use in pies, apple crisp desserts and applesauce. The variety has not to date been used for juice production.

Chart A

Sensory evaluations of apple cultivars harvested by the University of Minnesota Horticultural Research Center. Excelsior, Minnesota. Fruit was evaluated by a trained sensory panel. The rating scale ranged from 1 = low to 9 = high.

| Cultivar | Skin Color | Flesh Color | Flavor/ Aroma | Testure Rating | General |
|---|---|---|---|---|---|
| November 1985 (1985 Crop) | | | | | |
| Honeycrisp | 6.2 | 5.7 | 6.6 | 7.2 | 6.4 |
| Honeygold | 6.2 | 6.3 6.7 | 6.3 | 6.4 | |
| Regent | 7.5 | 7.9 | 6.1 | 6.6 | 6.5 |
| Haralson | 6.9 | 7.4 | 6.3 | 6.3 | 6.5 |
| February 1986 (1985 Crop) | | | | | |
| Honeycrisp | 6.4 | 6.0 | 5.6 | 7.2 | 6.0 |
| Honeygold | 5.6 | 5.4 | 4.4 | 4.2 | 5.0 |
| Regent | 6.8 | 5.6 | 5.8 | 6.2 | 5.6 |
| Haralson | 5.7 | 5.5 | 5.1 | 6.0 | 5.1 |
| Keepsake | 5.7 | 5.2 | 5.5 | 6.5 | 5.5 |
| November 1986 (1986 Crop) | | | | | |
| Honeycrisp | 6.6 | 6.1 | 6.7 | 7.1 | 6.8 |
| Macspur | 6.8 | 6.7 | 5.9 | 5.0 | 5.7 |
| Regent | 6.0 | 6.5 | 6.0 | 5.2 | 5.3 |
| Haralson | 6.9 | 6.4 | 6.9 | 6.2 | 6.2 |
| Gold. Delic. | 5.8 | 6.1 | 7.1 | 6.3 | 6.6 |
| February 1987 (1987 Crop) | | | | | |
| Honeycrisp | 6.4 | 6.6 | 7.4 | 7.0 | 6.8 |
| Regent | 6.8 | 7.2 | 5.4 | 5.2 | 5.6 |
| Haralson | 6.8 | 4.4 | 4.6 | 4.6 | 4.6 |
| Keepsake | 5.8 | 4.8 | 5.2 | 5.4 | 4.8 |
| November 1987 (1987 Crop) | | | | | |
| Honeycrisp | 6.0 | 6.0 | 6.3 | 7.5 | 6.7 |
| Honeygold | 6.2 | 7.0 | 5.3 | 6.4 | 5.6 |
| Regent | 6.5 | 7.5 | 6.6 | 7.2 | 6.8 |
| McIntosh | 7.3 | 7.2 | 6.8 | 5.2 | 6.1 |
| Haralson | 6.3 | 6.6 | 5.4 | 6.7 | 6.0 |

Chart B

Average injury rating of 1-year old wood collected at the University of Minnesota Horticultural Research Center and subjected to laboratory freezing tests on two dates: (1) December 30, 1986 frozen to temperatures of −28 to −40° F.; (2) January 22, 1988 frozen to temperatures of −33 to −42° F. Rating scale ranges from 1 = no injury to 5 = dead.

| Cultivar | Injury Rating 12-86 | Injury Rating 1-88 |
|---|---|---|
| Honeycrisp | 2.0 | 2.9 |
| McIntosh | 1.6 | 3.3 |
| Regent | 2.9 | 2.3 |
| State Fair | 1.7 | 2.9 |
| Honeygold | 2.8 | 3.1 |
| Haralson | 2.3 | 2.7 |

I claim:

1. A new and distinct apple tree substantially as shown and described particularly characterized by a superior fruit with a crisp and juicy texture, an extended season of harvest but with generally even ripening of fruit whereby repeat pickings are unnecessary, a moderately vigorous growth, little winter injury, annual fruit production and with no flower thinning required.

* * * * *

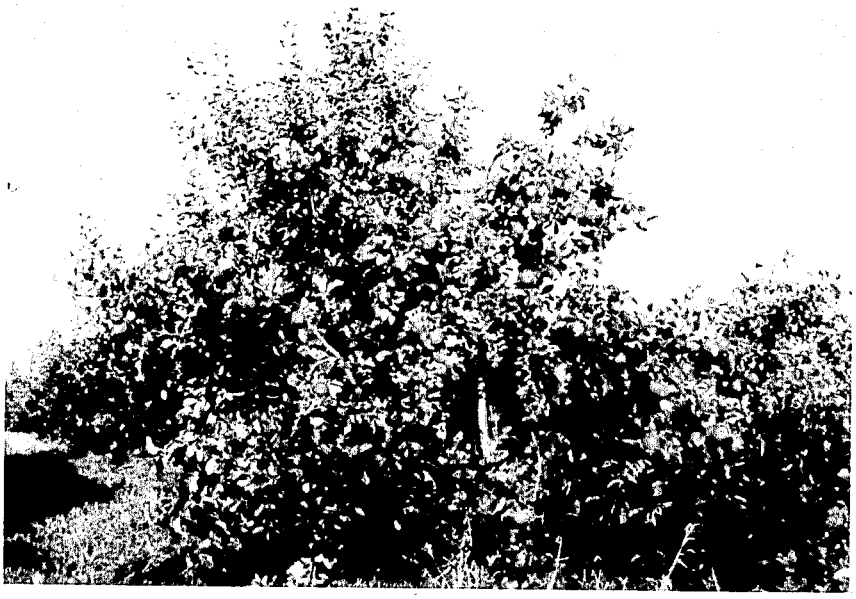
FIG.1
FIG.2
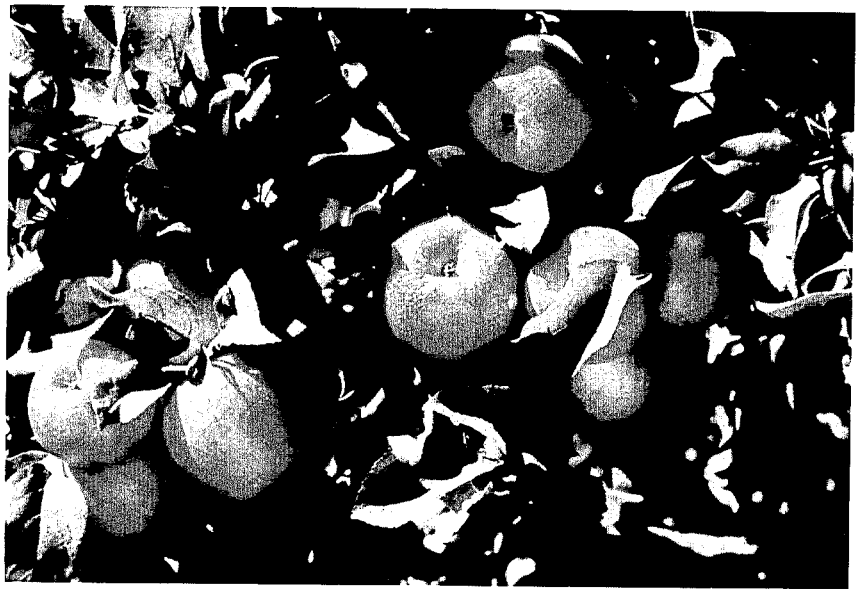

UNITED STATES PATENT AND TRADEMARK OFFICE

CERTIFICATE OF CORRECTION

PATENT NO. : Plant 7,197

DATED : March 20, 1990

INVENTOR(S) : Jim Luby and David Bedford

It is certified that error appears in the above-identified patent and that said Letters Patent is hereby corrected as shown below:

Col. 2, line 8
"Harlson" should be --Haralson--

Col. 3, line 47
"The" should begin a new paragraph.

Col. 4, Chart A, line 2
after "Center" change the period to a comma.

Col. 4, line 9 of Chart A
beginning with "6.7" move the numbers over 1 column.

Col. 4, Chart A, line 14
"5.6" should be --5.8--.

Col. 4, Chart A, line 22
"6.2" should be --6.3--.

Col. 4, Chart A, line 24
"1987" should be --1986--.

Signed and Sealed this

Thirty-first Day of December, 1991

*Attest:*

*Attesting Officer*

HARRY F. MANBECK, JR.

*Commissioner of Patents and Trademarks*